(12) United States Patent
Kohno

(10) Patent No.: US 8,177,717 B2
(45) Date of Patent: May 15, 2012

(54) ULTRASONIC ENDOSCOPE

(75) Inventor: Shinichi Kohno, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 376 days.

(21) Appl. No.: 11/723,689

(22) Filed: Mar. 21, 2007

(65) Prior Publication Data
US 2007/0249940 A1 Oct. 25, 2007

(30) Foreign Application Priority Data

Mar. 22, 2006 (JP) .................. P2006-078062

(51) Int. Cl.
*A61B 8/00* (2006.01)
*A61B 1/04* (2006.01)

(52) U.S. Cl. ........................ 600/437; 600/116

(58) Field of Classification Search ............... 600/463
See application file for complete search history.

(56) References Cited

U.S. PATENT DOCUMENTS

| 6,149,598 | A | 11/2000 | Tanaka |
| 6,186,947 | B1 | 2/2001 | Ouchi |
| 6,238,336 | B1 | 5/2001 | Ouchi |
| 6,338,717 | B1 | 1/2002 | Ouchi |
| 2004/0082883 | A1* | 4/2004 | Kohno .................. 601/2 |
| 2004/0186514 | A1* | 9/2004 | Swain et al. ............. 606/224 |

FOREIGN PATENT DOCUMENTS

| DE | 199 39 109 A1 | 2/2000 |
| JP | 5-56912 A | 3/1993 |
| JP | 8-126644 A | 5/1996 |
| JP | 9-108224 A | 4/1997 |
| JP | 09122067 | * 5/1997 |
| JP | 11-276422 A | 10/1999 |
| JP | 2000060856 | * 2/2000 |
| JP | 2001-340344 A | 12/2001 |
| JP | 2004-135937 A | 5/2004 |

OTHER PUBLICATIONS

Office Action in Japanese Application No. 2006-078062 mailed Apr. 21, 2011, including an English translation.

* cited by examiner

*Primary Examiner* — Tse Chen
*Assistant Examiner* — Hien Nguyen
(74) *Attorney, Agent, or Firm* — Birch, Stewart, Kolasch & Birch, LLP

(57) ABSTRACT

An ultrasonic endoscope comprising an insertion portion including a distal hard portion. The insertion portion comprises an ultrasonic transducer arranged in the distal hard portion and a treatment equipment lead-out hole, a slant surface on which an endoscopic viewing section is formed, the slant surface being provided in a position rear of the treatment equipment lead-out hole and a balloon removably arranged in a fit area on the ultrasonic transducer. The distal hard portion comprises a balloon-fit groove between an arrangement region of the ultrasonic transducer and an opening of the treatment equipment lead-out hole. The balloon has an end including a retaining ring that fits in the balloon-fit groove. The distal hard portion further comprises a treatment equipment guide member that slidably guides the treatment equipment across an arrangement area of the balloon-fit groove and up to a position on a beginning side of a scanning range of the ultrasonic transducer.

5 Claims, 4 Drawing Sheets

ULTRASONIC ENDOSCOPE

BACKGROUND OF THE INVENTION

1. Field of the Invention

The present invention relates to an ultrasonic endoscope arranged with an ultrasonic transducer and an endoscopic viewing section at the distal end of an insertion portion to be inserted in a body cavity, and more particularly to an ultrasonic endoscope adapted to fit a balloon on the ultrasonic transducer.

2. Description of the Related Art

The ultrasonic endoscope has an insertion portion to be inserted in a body cavity. The insertion portion has a distal hard portion incorporating ultrasonic examining means and endoscopic viewing means therein. The endoscopic viewing means is made up with an illuminating device and a viewing device. The viewing device usually has a solid-state imager. Meanwhile, the ultrasonic examining means is made up by an ultrasonic transducer. The ultrasonic transducer is to transmit an ultrasonic wave toward a body interior and receive a reflection echo from a tissue laminagraphic point, thereby acquiring information about a body-interior tissue. The ultrasonic transducer is to make a scanning mechanically or electronically over a predetermined range, thereby allowing diagnosis, e.g. finding out a diseased point in the body interior.

Here, conspicuous attenuations are encountered through air in the ultrasonic signal sent from the ultrasonic transducer into a body interior and in the reflection echo of from a laminagraphic point of a body-interior tissue. In order to interpose an ultrasonic transmission medium between the ultrasonic transducer and the wall of a body cavity, a balloon is fit on the distal hard portion where the ultrasonic transducer is arranged. The balloon is filled therein with an ultrasonic transmission medium and inflated a predetermined amount under the pressure thereof. By placing the balloon in abutment against a body-cavity wall, air is prevented from existing along the transmission and reception paths of an ultrasonic wave.

Here, when confirmed a presence of a point assumed as a diseased as a result of the ultrasonic examination, tissue cells are sampled out of the point by use of a needle tool, thereby conducting an exact examination. Meanwhile, when confirmed as a diseased point, it is treated by injecting a liquid agent or so, wherein the needle tool is also used for this purpose. The needle tool is sharpened at its tip because to be inserted in a body interior. In the event the needle tool goes into contact with the balloon in an inflated state, the balloon results into burst. Accordingly, there is a need to operate the needle tool in a manner not to contact the balloon.

JP-A-5-56912 discloses a structure whose balloon is not to be damaged by a needle tool, in a structure that an ultrasonic endoscope is fit with a balloon on a distal hard portion thereof in a region where an ultrasonic transducer is arranged, and provided with a treatment equipment lead-out hole in a position rear of the balloon-fit area so that the needle tool can be projected out of the treatment equipment lead-out hole thereby performing a treatment, such as cell sampling. In JP-A-5-56912, a treatment equipment rising device is provided in the distal hard portion so that the rising device can regulate the angle of the needle tool projecting out of the treatment equipment lead-out hole into a direction not to contact the inflated balloon.

In JP-A-5-56912, the rising device for regulating the direction of the treatment equipment is provided in the interior of the treatment equipment lead-out hole. The treatment equipment lead-out hole is spaced from the arrangement region of the ultrasonic transducer because it is arranged rear of the balloon-fit area. Here, in order to ensure a safe treatment with the needle tool, the needle tool is arranged to be monitored through the endoscopic viewing means in the stage before inserted in a body interior, and monitored through the ultrasonic examining means after inserted in the body interior. However, where the treatment equipment lead-out hole and the ultrasonic transducer are spaced in position, there is a need to increase the region where the needle tool is to be monitored by the endoscopic viewing means wherein the needle tool is not allowed to be inserted in a body interior until reaching the scanning range of the ultrasonic transducer. This increases the distance required for the needle tool to reach from the treatment equipment lead-out hole to an insertion point into a body interior, during which the needle tool at its tip is placed in a free state without being given any guide. This problematically results in a lowered shootability of the treatment equipment to a diseased point, etc.

SUMMARY OF THE INVENTION

The present invention has been made in view of the foregoing point, and it is an object thereof to provide an ultrasonic endoscope improved in the directional controllability and shootability of its needle tool projecting out of the treatment equipment lead-out hole.

In order to achieve the foregoing object, an ultrasonic endoscope comprising: an insertion portion including a distal hard portion, the insertion portion comprising: an ultrasonic transducer arranged in the distal hard portion; a treatment equipment lead-out hole that allows a treatment equipment to project in a direction toward an obliquely forward from a rear point of the ultrasonic transducer; a slant surface on which an endoscopic viewing section is formed, the slant surface being provided in a position rear of the treatment equipment lead-out hole; and a balloon removably arranged in a fit area on the ultrasonic transducer; wherein the distal hard portion comprises a balloon-fit groove between an arrangement region of the ultrasonic transducer and an opening of the treatment equipment lead-out hole; the balloon has an end including a retaining ring that fits in the balloon-fit groove; and the distal hard portion further comprises a treatment equipment guide member that slidably guides the treatment equipment, projecting out of the treatment equipment lead-out hole, across an arrangement area of the balloon-fit groove and up to a position on a beginning side of a scanning range of the ultrasonic transducer.

The ultrasonic transducer is of a mechanical scanning type or an electronic scanning type, wherein scanning is desirably provided in direction, e.g. can be linear, convex or radial in direction. In any case, although scanning is to be made over a predetermined range, the treatment equipment guide member is provided not to overlap with the scanning range of such a ultrasonic wave but extendable up to a point close to the ultrasonic-wave scanning range. The balloon, to be fit on the ultrasonic transducer, uses a bag-type one or a cylindrical-type one. In order to fit the balloon, a balloon-fit groove is provided in the distal hard portion. Where the balloon is in a bag type, the balloon-fit groove is formed in an area between the arrangement region of the ultrasonic transducer and the treatment equipment lead-out hole. Meanwhile, where a cylindrical balloon is used, balloon-fit grooves are provided in two regions, i.e. in front-side and rear-side areas relative to the ultrasonic transducer. In any case, the treatment equipment guide member has a length of at least up to a point beyond the balloon-fit groove in the rear-side position, preferably extending up to a vicinity of the arrangement area of the ultrasonic transducer.

The treatment equipment receiving passage is structured by a treatment equipment receiving tube extending to a rear point of the distal hard portion of the insertion portion, i.e., on an angle region side, extending axially of the insertion portion. In the distal hard portion, a treatment equipment receiving passage is formed toward the obliquely forward. The treatment equipment receiving tube and the treatment equipment receiving passage are connected together by a connection pipe. The connection pipe is in a curved form, thus making it possible to change the direction of the treatment equipment in the region of the connection pipe. Accordingly, the treatment equipment, particularly a needle tool having a needle portion at its tip for example, is tend to assume straight when projected out of the treatment equipment lead-out hole. For this reason, the treatment equipment guide member has a guide surface that guides the treatment equipment along the lower surface of a path of the treatment equipment receiving passage directed obliquely upward. The treatment equipment, as moved forward, is directed away from the arrangement region of the ultrasonic transducer.

As described above, the treatment equipment guide member avoids the distal hard portion of the insertion portion from increasing in length, by covering a part of the balloon-fit groove. Accordingly, without a change, the balloon is difficult to fit. For this reason, the treatment equipment guide member can be made rotatively displaceable a treatment equipment guide position where covering the balloon-fit groove and a groove-open position where spaced from the balloon-fit groove. Meanwhile, the distal hard portion is desirably provided with a stopper that positions the treatment equipment guide member in the treatment equipment guide position. Here, the treatment equipment guide member may be displaced by sliding between the treatment equipment guide position and the groove-open position. However, it can be by rotation advantageously in respect of space. The treatment equipment guide member is desirably reacted upon by a spring wherein the treatment equipment guide member has a support portion that supports in a direction abutting against the stopper, the support means being structured to release, by manual operation, from supporting the treatment equipment guide member into displacement to the groove-open position. When fitting a balloon, the treatment equipment guide member is held in the groove-open position by a click portion. When placing it in the treatment equipment guide position, engagement is satisfactorily released from the click portion.

DETAILED DESCRIPTION OF THE INVENTION

Figure 1:
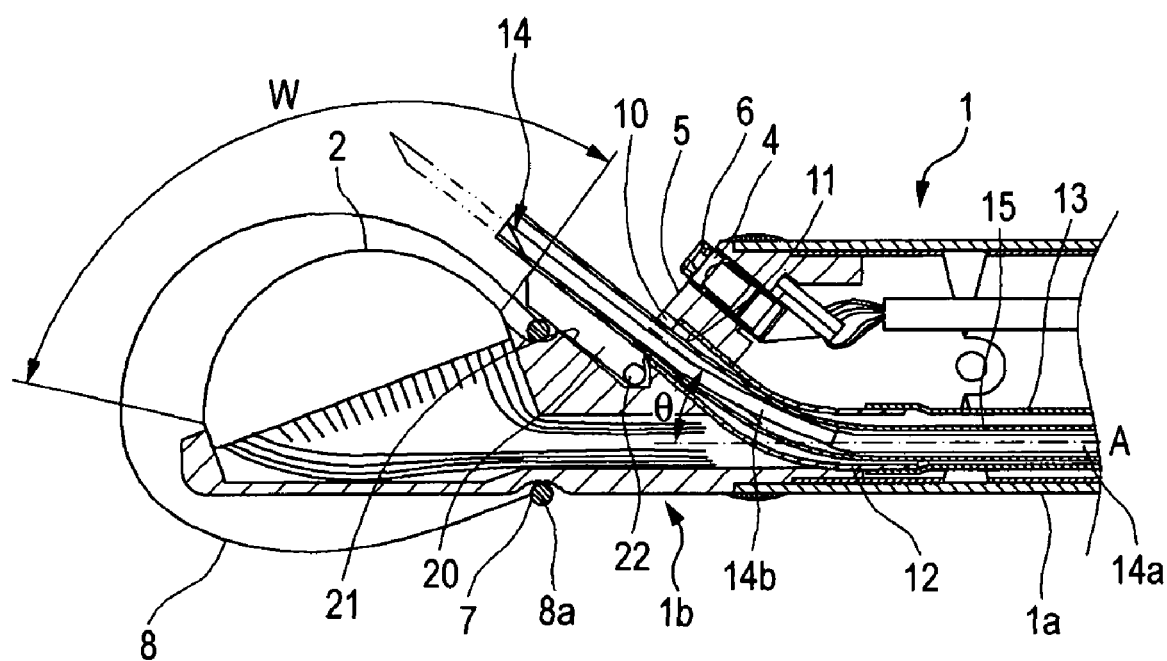
FIG. 1 is a sectional view of a distal end portion of an insertion portion of an ultrasonic endoscope.
Figure 2:
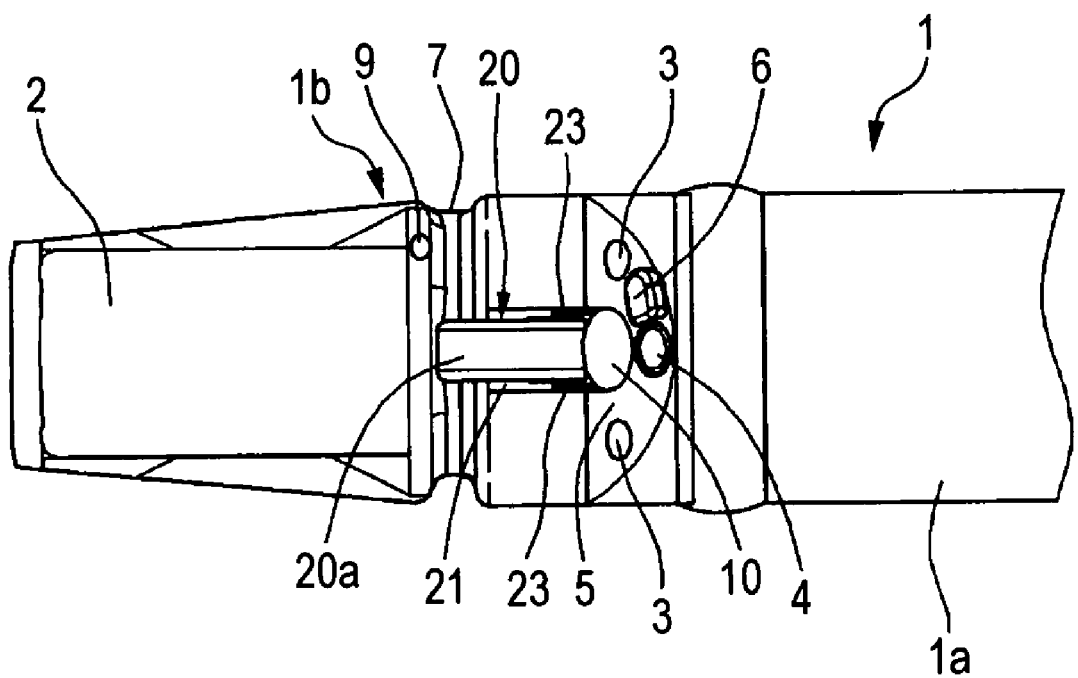
FIG. 2 is a plan view of the distal end portion of the insertion portion.
Figure 3:
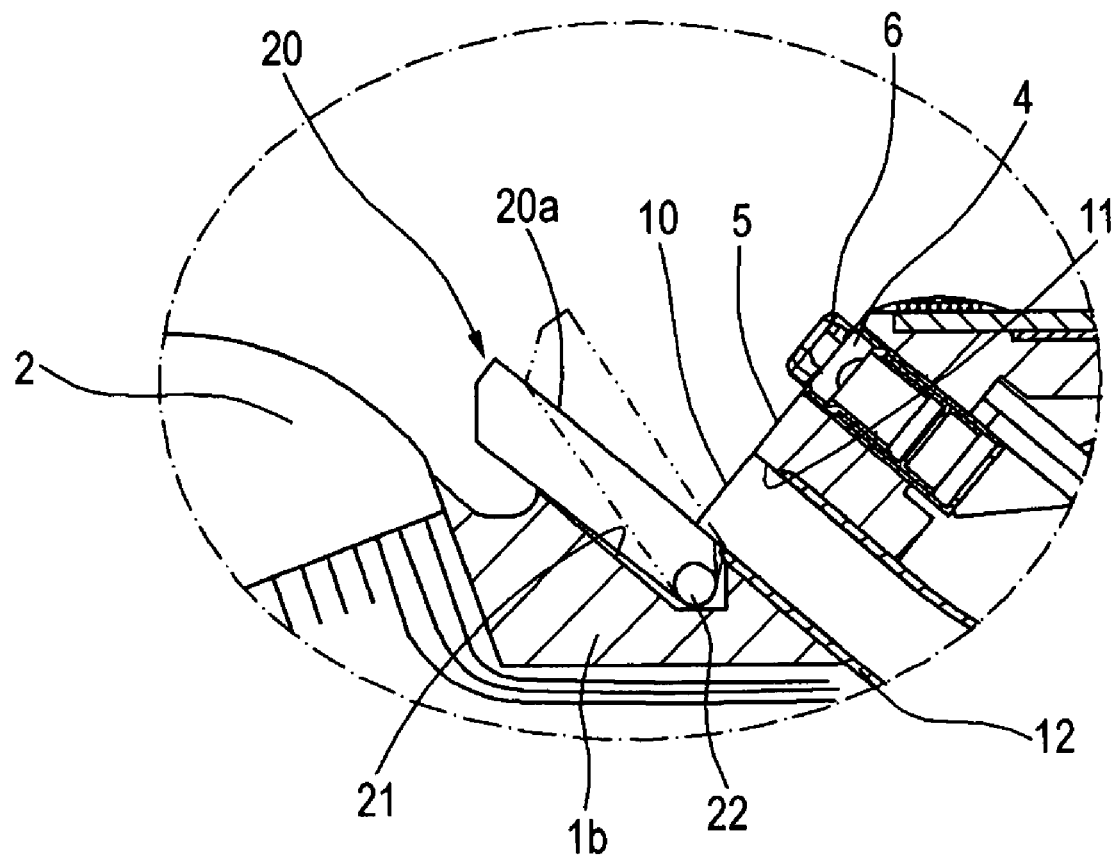
FIG. 3 is an essential-part magnifying view of FIG. 1, showing a state not to pass a needle tool.
Figure 4:
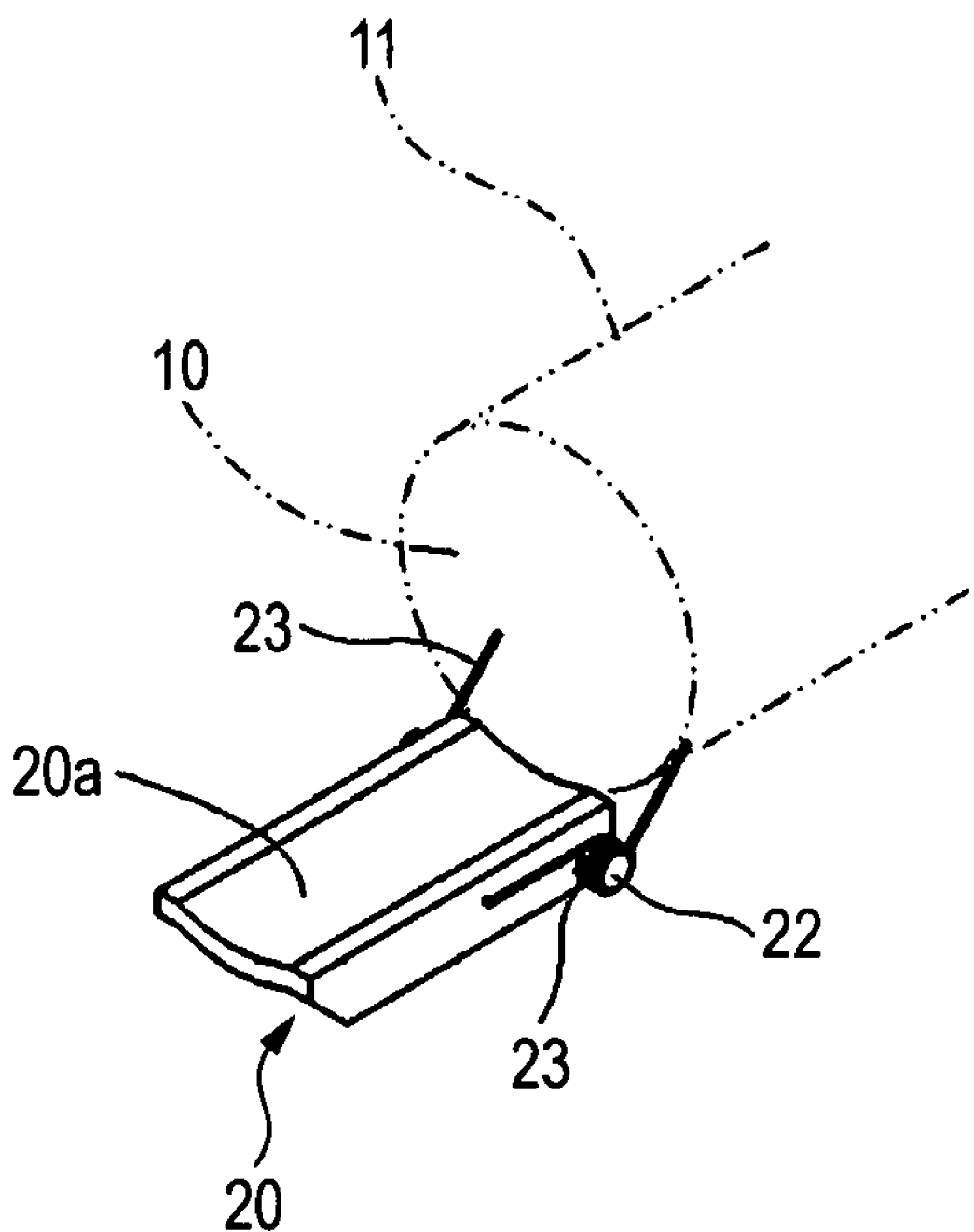
FIG. 4 is an explanatory view showing a structure of a treatment equipment guide member for a treatment equipment.

Based upon the drawings, explanation will now be made on an embodiment according to the present invention. FIG. 1 shows a sectional structure of an ultrasonic endoscope at the distal end portion of its insertion portion while FIG. 2 shows a plan structure of the distal end portion. FIG. 3 is a magnifying view of an essential part of FIG. 1, illustrating a state not passing a needle tool.

As apparent from the figures, an ultrasonic examining section and an endoscopic viewing section are provided at a distal hard portion 1b provided connected to an angle region 1a of the insertion portion 1. The ultrasonic examining section illustrated is made by an ultrasonic transducer 2 arranged with a multiplicity of ultrasonic vibrators axially of the distal hard portion 1b. The ultrasonic vibrators, constituting the ultrasonic transducer 2, are arranged extending from a point close to the tip of the distal hard portion 1b toward an axially-rear of the distal hard portion 1b and, moreover, made in a convex form with respect to the axial direction. The ultrasonic vibrators, arranged in multiplicity to constitute the transducer 2, are to be driven sequentially, which enables convex-ultrasonic electronic scanning over the range shown at W in FIG. 1.

Meanwhile, the endoscopic viewing section is structured with an illuminating device 3 and a viewing device 4, as apparent from FIG. 2, which are formed in a slant surface 5 formed in the rear end of the distal hard portion 1b. The illuminating device 3 and the viewing device 4 are provided in the slant surface 5. The viewing device 4 is arranged nearly intermediate in the slant surface 5, and made up by an objective optical system and solid-state imaging section provided at a focal point of the objective optical system. The illuminating device 3 is formed two at left and right sandwiching the viewing device 3, and structured with an optical fiber to convey the illumination light from a light source that the ultrasonic endoscope is removably connected and diffusion lenses attached on the illuminating device 3. Furthermore, a cleaning nozzle 6 is arranged to eject a cleaning fluid toward the viewing device 4.

Here, a balloon-fit groove 7 is formed circumferentially in the distal hard portion 1b in an area rear of the arrangement of the ultrasonic transducer 2, as shown in FIG. 1. A balloon 8 is removably attached in the balloon-fit groove 7. The balloon 8 is in a bag form, whose opening end is formed with a retaining ring 8a. The retaining ring 8a, elastic in nature, has a diameter smaller than the groove-bottom diameter of the balloon-fit groove 7, so that it can be received in the balloon-fit groove 7 in a manner the retaining ring 8 is spread in its diameter. In the distal hard portion 1b, a supply passage 9 (FIG. 2) for an ultrasonic transmission medium is opened in a position closer to the tip than the position the balloon-fit groove 7 is formed.

In the slant surface 5 arranged with the illuminating device 3 and the viewing device 4, a treatment equipment lead-out hole 10 is opened, for the viewing device 4, in a position closer to the tip axially of the distal hard portion 1b. The treatment equipment lead-out hole 10 forms an opening end of a passage to receive therein the treatment equipment arranged in the insertion portion 1. Namely, the distal hard portion 1b is opened with a treatment equipment receiving passage 11 such that it inclines obliquely frontward. The treatment equipment receiving passage 11 receives therein a connection pipe 12 at its tip portion. Meanwhile, the connection pipe 12 has a rear portion connected with a treatment equipment receiving tube 13, which tube 13 extends throughout the entire length of the insertion portion 1.

The insertion portion 1 is to bend along a passage where inserted, whose angle region 1a is structured to bend by manual operation. The treatment equipment receiving tube 13 is flexible in bending so that, when the insertion portion 1 is bent along a passage where inserted or the angle region 1a is operated to bend, the treatment equipment receiving tube 13 bends in a following manner. However, as apparent from FIG.

1, when the insertion portion 1 is in a straight state, the treatment equipment receiving tube 13 extends axially of the insertion portion 1. Meanwhile, the treatment equipment receiving passage 11 has a predetermined angle θ relative to the axis A thereof. Accordingly, the connection pipe 12 is in a form curving at the intermediate thereof. Due to this, the treatment equipment extends from the treatment equipment receiving tube 13 to the treatment equipment receiving passage 11 in a manner changed in direction into an angle θ by the connection pipe 12, thus going out of the treatment equipment lead-out hole 10.

The treatment equipment, for use in the ultrasonic endoscope, may be a needle tool 14 shown in FIG. 1. The needle tool 14 is connected with a needle 14b at the tip of its flexible tube 14a. The needle 14b is formed by a rigid pipe, such as a metal pipe, having a tip sharpened in order to be inserted in a body interior. For this reason, the needle tool 14 is received in a protection sleeve 15 in order to prevent the treatment equipment receiving tube 13 and the inner wall of a body cavity from being damaged by the tip of the needle 14b when it is inserted in the treatment equipment receiving tube 13 or when projected out of the treatment equipment lead-out hole 10. As apparent from FIG. 1, by placing the needle 14b of the needle tool 14 in a state not projecting out of the tip of the protection sleeve 15, its tip is projected up to a predetermined position from the treatment equipment lead-out hole 10. The protection sleeve 15 is guided preferably into contact with a body-cavity wall or to a position slightly in front thereof. Thereafter, as shown by the virtual lines in the figure, the needle tool 14 positioned in the protection sleeve 15 is moved in a manner pushed out of the tip of the protection sleeve 15. The needle 14b is projected out of the treatment equipment lead-out hole 10 and then inserted into a body-cavity wall.

A treatment equipment guide member 20 is provided nearby the opening of the treatment equipment lead-out hole 10. The treatment equipment guide member 20 is arranged between the arrangement region of the viewing device 4 and the arrangement region of the ultrasonic transducer 2, in a receiving space provided in an area close to the ultrasonic transducer 2. Here, the receiving space 21 is formed in the distal hard portion 1b in a manner cutting its surface away. The treatment equipment guide member 20, arranged in the receiving space 21, has a guide surface 20a to slidably guide the treatment equipment projecting out of the treatment equipment lead-out hole 10. The guide surface 20a is made, widthwise, as an arcuate surface nearly matched to the treatment equipment receiving passage 11. In order to secure the stability of the treatment equipment, the arcuate angle thereof has at least 30 degrees.

The treatment equipment guide member 20 is to guide the treatment equipment in the distal hard portion 1b, toward the obliquely forward of and across the balloon-fit groove 7. By thus extending the treatment equipment guide section up to the frontward than the balloon-fit groove 7, the treatment equipment is improved in shootability to a diseased part, etc. without increasing the length of the distal hard portion 1b. However, the treatment equipment guide member 20 is given a length that the tip thereof does not reach the inside of a scanning range W of the ultrasonic transducer 2, preferably extending up to a point nearly coincident with a delimitation of the scanning range W. In this manner, the treatment equipment guide member 20, if not modified, is obstructive to the fitting of the retaining ring 8a into the balloon-fit groove 7 because it covers a part of the balloon-fit groove 7.

Due to the foregoing, the treatment equipment guide member 20 is rotatably supported in the distal hard portion 1b through a pivot shaft 22 so that the tip thereof can rotatively move in a direction toward and away from the receiving space 21. In order to stably hold the treatment equipment guide member 20 in the receiving space 21, springs 23 are fit on the pivot shaft 22 of the treatment equipment guide member 20. By means of the springs 23, the treatment equipment guide member 20 is placed in abutment against a surface of the receiving space 21. This state provides a treatment equipment guide position as shown by the solid lines in FIG. 3. By rotating the treatment equipment guide member 20 against the force of the springs 23 up to a position shown by the virtual lines in FIG. 3, the balloon-fit groove 7 is opened in above thereof so that the balloon 8 can be attached. This provides a full-open position.

Accordingly, the surface of the receiving space 21 serves as a stopper that positions the treatment equipment guide member 20 in its guide position. The springs 23 put the treatment equipment guide member 20 in abutment against the surface of the receiving space 21. The guide surface 20a provides support portion that supports the treatment equipment in a state nearly continuous with the treatment equipment receiving passage 11. At this time, the treatment equipment guide member 20 covers the balloon-fit groove 7 wherein the guide surface 20a provides an arcuate surface nearly continuous with the treatment equipment receiving passage 11.

By inserting the ultrasonic endoscope thus structured into the body interior of a subject-of-examination through attaching the balloon 8 thereon, endoscopic and ultrasonic examinations or diagnosis can be conducted. Where there is any change, say, in a body-cavity wall, e.g. a swell occurrence or a color change, as a result of the endoscopic examination on a body interior through the viewing device 4, ultrasonic examination is conducted on the relevant point. In the ultrasonic examination, the balloon 8 is first inflated by supplying an ultrasonic transmission medium into the balloon 8 through the supply passage 9, the balloon 8 at its surface is placed in abutment against a body-cavity wall. In this state, an ultrasonic wave is transmitted from the ultrasonic transducer 2, to receive a reflection echo signal of from a body-tissue laminagraphic region. Based upon the reflection echo, an ultrasonic image is generated and displayed on a monitor. In case a possibly diseased point is detected as a result of the ultrasonic examination, the needle tool 14 is used to sample the tissue.

In the protection sleeve 15, previously incorporated in a retracted position is the needle 14b of the needle tool 14 to guide in the treatment equipment receiving passage 11. The needle tool 14 is inserted from the treatment equipment receiving tube 13 into the connection pipe 12, thus being extended up to the connection pipe 12 or to the treatment equipment receiving passage 11 beyond the same. This operation can be conducted after detecting a possibly diseased point.

In performing a treatment such as tissue sampling, the entire needle tool 14 including the needle 14b is projected out of the treatment equipment lead-out hole 10 while being received in the protection sleeve 15. Due to this, the protection sleeve 15 tip moves from the treatment equipment lead-out hole 10 onto the guide surface 20a of the treatment equipment guide member 20 where it is guided along the guide surface 20a into a forward movement while sliding the surface thereof. In this manner, the protection sleeve 15 receiving therein the needle tool 14 is guided by the treatment equipment guide member 20 over a long distance of up to a point, nearly coincident with the delimitation of the scanning range W of the ultrasonic transducer 2, beyond the balloon-fit groove 7 fit with the retaining ring 8a of the balloon 8. The needle tool 14 is easily controlled in its direction, thus ensuring the correct shootability without increasing the total length of the distal hard portion 1b.

In this manner, the needle tool 14, sharpened at its tip, is guided by the treatment equipment guide member 20 until passing the retaining ring 8a of the balloon 8. Moreover, because the treatment equipment guide member 20 is a thick-walled member, the needle 14b of the needle tool 14 is allowed to move toward a body-cavity wall in a state positively spaced from the balloon 8. Accordingly, there is no fear that the protection sleeve 15 or the needle 14b contacts the balloon 8, thus eliminating the inconvenience of damaging the balloon 8 or so.

Meanwhile, in the prior stage to an insertion to a body-cavity wall, the needle tool 14 is operated under monitor of the viewing device 4. While the needle tool 14 at its tip is on the guide surface 20a of the treatment equipment guide member 20, it positions within the protection sleeve 15 as shown by the solid line in FIG. 1. When the protection sleeve 15 advanced to a point of insertion within the body cavity or to a point immediately in front thereof, the needle 14b of the needle tool 14 is projected out of the protection sleeve 15 tip as shown in the virtual lines in the figure. As soon as the needle 14b is inserted in the body-cavity wall, it becomes a state that capture is possible in the field-of-view of the ultrasonic transducer 2. Namely, there is no possibility of becoming so-called a blind state that the tip of the needle tool 14 is not covered by the field-of-view of the viewing device 4 nor the field-of-view of the ultrasonic transducer 2.

After the use of the ultrasonic endoscope, the balloon 8 is removed. Before a start of use, a new balloon 8 is attached. When removing or attaching the balloon 8, the treatment equipment guide member 20 covering the balloon-fit groove 7 is pushed up by a finger and rotated about the rotary shaft 22 against the force of the spring 23. This places the treatment equipment guide member 20 in a groove-open position that is spaced from the receiving space 21 of the distal hard portion 1b. As a result, the balloon 8 can be attached and removed with smoothness. By releasing the treatment equipment guide member 20 from the operation force, the treatment equipment guide member 20 becomes covering the balloon-fit groove 7 through the action of the spring 23, thus being returned into a treatment equipment guide position where the guide surface 20a lies in an extension position of the treatment equipment receiving passage 11.

The needle tool, received in the treatment equipment receiving passage, can be put in a field-of-view of the endoscopic viewing section until immediately before it is inserted in a body interior. As soon as it is inserted in the body interior, capture can be in a field-of-view by means of the ultrasonic transducer, thus improving the operation safety of the needle tool. Because of guided up to immediately before an insertion in a body interior by the treatment equipment guide member, the treatment equipment is improved in directional controllability and shootability.

The entire disclosure of each and every foreign patent application from which the benefit of foreign priority has been claimed in the present application is incorporated herein by reference, as if fully set forth.

What is claimed is:

1. An ultrasonic endoscope comprising an insertion portion including a distal hard portion,
the insertion portion comprising:
an ultrasonic transducer arranged in the distal hard portion;
a treatment equipment lead-out hole that allows a treatment equipment to project in a direction toward an obliquely forward from a rear point of the ultrasonic transducer;
a slant surface on which an endoscopic viewing section is formed, the slant surface being provided in a position rear of the treatment equipment lead-out hole; and
a balloon removably arranged in a fit area on the ultrasonic transducer;
wherein the distal hard portion comprises a balloon-fit groove between an arrangement region of the ultrasonic transducer and an opening of the treatment equipment lead-out hole;
the balloon has an end including a retaining ring that fits in the balloon-fit groove; and
the distal hard portion further comprises a treatment equipment guide member that slidably guides the treatment equipment, projecting out of the treatment equipment lead-out hole, across an arrangement area of the balloon-fit groove and up to a position on a beginning side of a scanning range of the ultrasonic transducer,
wherein the treatment equipment guide member is allowed to rotatively displace between
a treatment equipment guide position, wherein the treatment equipment guide member covers the balloon-fit groove and
a groove-open position, wherein the treatment equipment guide member is spaced from the balloon-fit groove in order to install the balloon, and
the distal hard portion comprises a stopper that positions the treatment equipment guide member in the treatment equipment guide position.

2. The ultrasonic endoscope according to claim 1,
wherein the treatment equipment guide member comprises a support portion that supports the treatment equipment guide member in a direction abutting against the stopper, and
the support portion is structured to release, by manual operation, from supporting the treatment equipment guide member to the groove-open position.

3. The ultrasonic endoscope according to claim 1, wherein the treatment equipment which is projected from the treatment equipment lead-out hole shoots in the scanning range of the ultrasonic transducer.

4. The ultrasonic endoscope according to claim 1, wherein the treatment equipment which is projected from the treatment equipment lead-out hole is guided by the treatment equipment guide member until passing the retaining ring of the balloon.

5. The ultrasonic endoscope according to claim 1,
wherein the treatment equipment guide member extends up to a point coincident with a delimitation of the scanning range of the ultrasonic transducer,
a front area of the insertion portion includes the ultrasonic transducer and the balloon,
a rear area of the insertion portion includes the treatment equipment lead-out hole, the viewing window and the illuminating window, and
the ultrasonic transducer and the viewing window sandwich the transducer equipment lead-out hole.

* * * * *